United States Patent
Karim et al.

(10) Patent No.: US 9,526,466 B2
(45) Date of Patent: Dec. 27, 2016

(54) MULTI-LAYER FLAT PANEL X-RAY DETECTOR

(75) Inventors: Karim S. Karim, Waterloo (CA); Nicholas Allec, Waterloo (CA)

(73) Assignee: UNIVERSITY OF WATERLOO, Waterloo (CA)

(*) Notice: Subject to any disclaimer, the term of this patent is extended or adjusted under 35 U.S.C. 154(b) by 233 days.

(21) Appl. No.: 13/380,127

(22) PCT Filed: Jul. 16, 2010

(86) PCT No.: PCT/CA2010/001113
§ 371 (c)(1),
(2), (4) Date: Dec. 22, 2011

(87) PCT Pub. No.: WO2011/006257
PCT Pub. Date: Jan. 20, 2011

(65) Prior Publication Data
US 2012/0106698 A1    May 3, 2012

Related U.S. Application Data

(60) Provisional application No. 61/213,795, filed on Jul. 16, 2009.

(51) Int. Cl.
| G01T 1/00 | (2006.01) |
| A61B 6/00 | (2006.01) |
| G01T 1/29 | (2006.01) |
| H01L 27/146 | (2006.01) |

(52) U.S. Cl.
CPC ............ *A61B 6/482* (2013.01); *A61B 6/4241* (2013.01); *A61B 6/502* (2013.01); *G01T 1/2928* (2013.01); *H01L 27/14663* (2013.01); *A61B 6/4488* (2013.01)

(58) Field of Classification Search
CPC ..... A61B 6/4241; A61B 6/482; G01T 1/2928; G01T 1/242
See application file for complete search history.

(56) References Cited

U.S. PATENT DOCUMENTS

| 4,247,774 A | 1/1981 | Brooks |
| 5,099,128 A | 3/1992 | Stettner |
| 5,138,167 A | 8/1992 | Barnes |
| 7,081,627 B2 * | 7/2006 | Heismann et al. ...... 250/370.11 |
| 7,092,481 B2 | 8/2006 | Hoffman |

(Continued)

FOREIGN PATENT DOCUMENTS

JP    2008067933    3/2008

OTHER PUBLICATIONS

Goldan et al, In Unipolar Charge Sensing Using Frisch Grid Technique for Amorpghous Selenium Radiation Detectors, Proc. of SPIE, Aug. 2005, vol. 7079, No. 1.

(Continued)

*Primary Examiner* — David J Makiya
*Assistant Examiner* — Danielle Fox
(74) *Attorney, Agent, or Firm* — Gowling WLG (Canada) LLP; Jeffrey W. Wong

(57) ABSTRACT

There is provided a multi-layer flat panel detector comprising a first conversion layer, a second conversion layer, at least one printed circuit board for receiving signals generated by the first or second direct conversion layers, and a processor for processing the signals to produce an image being generated.

19 Claims, 7 Drawing Sheets

(56) References Cited

U.S. PATENT DOCUMENTS

| | | | |
|---|---|---|---|
| 7,260,174 B2* | 8/2007 | Hoffman | A61B 6/032 250/363.09 |
| 7,302,031 B2* | 11/2007 | Hjarn et al. | 378/37 |
| 7,304,308 B2* | 12/2007 | Cheung et al. | 250/370.09 |
| 7,315,028 B2* | 1/2008 | Mochizuki | 250/370.11 |
| 7,532,703 B2 | 5/2009 | Du et al. | |
| 7,573,040 B2* | 8/2009 | Tkaczyk | G01T 1/242 250/370.09 |
| 2002/0027201 A1* | 3/2002 | Agano | 250/370.11 |
| 2005/0259783 A1* | 11/2005 | Hoffman | 378/19 |
| 2006/0192087 A1* | 8/2006 | Kuszpet et al. | 250/214 R |
| 2009/0129538 A1* | 5/2009 | Tkaczyk | A61B 6/032 378/5 |

OTHER PUBLICATIONS

Safavian et al, Characterization of Current Programmed Amorphous Silicon Active Pixel Sensor Readout Circuit for Dual Mode Diagnostic Digital X-ray Imaging, Proc. of SPIE, Feb. 2009, vol. 7258, No. 1.

Wang et al., in Silicon X-ray Detector with Integrated Thin-Film Transistor for Biomedical Applications, IEEE Electron Device Letters, Feb. 2010, p. 147-149, vol. 31, No. 2.

Karellas et al, Breast Cancer Imaging: a Perspective for the Next Decade, in Medical Physics, Nov. 2008, p. 4878-4897, vol. 35, No. 11.

Bornefalk, Computer-aided Detection and Novel Mammography Imaging Techniques, Doctoral Thesis, 2006, Department of Physics, Royal Institute of Technology, Stockholm, Sweden.

Heismann et al., Technology and Image Results of a Spectral CT System, Proc. of SPIE, 2004, p. 52-59 vol. 5368.

Gauntt et al., X-ray Tube Potential, Filteration, and Detector Considerations in Duel-Energy Chest Radiography, Medical Physics, Feb. 1994, p. 203-218, vol. 21, No. 2.

Boone et al., Dual-energy Mammography: A Detector Analysis, Medical Physics, Jul./Aug. 1990, p. 665-675, vol. 17, No. 4.

Canadian Intellectual Property Office (ISA/CA), International Search Report and Written Opinion dated Oct. 25, 2010, International Application No. PCT/CA2010/001113, Gatineau, Quebec, Canada.

* cited by examiner

MULTI-LAYER FLAT PANEL X-RAY DETECTOR

CROSS-REFERENCE TO RELATED APPLICATIONS

The present application claims the benefit of U.S. provisional patent application No. 61/213,795, filed Jul. 16, 2009, which is incorporated herein by reference.

FIELD OF THE DISCLOSURE

The disclosure is directed generally at x-ray detectors and more specifically at a multi-layer flat panel x-ray detector.

BACKGROUND OF THE DISCLOSURE

In digital mammography (DM), a single image or several images of a body part, such as a breast, of a patient are taken at different angles using a high energy electromagnetic x-ray source and a single layer flat panel x-ray detector. These images are then used for the diagnosis or treatment of breast cancer or other disease.

Digital subtraction mammography (DSM) is a method of breast angiography wherein a contrast media is intravenously injected into a patient to enhance the acquired image. This method is used to visualize cancers that cannot be seen using standard DM, for example in breasts having a high density. It is also thought that using DSM enhances the visualization of calcifications and help in the monitoring and treatment of breast cancer.

During the development of cancer, the growth of new blood vessels occurs which is also known as tumor angiogenesis. With an increase in tumor cell population, new capillary growth accompanies an increase in tumor cell population to provide sufficient materials for cell proliferation. This property is used by DSM since cancers will absorb the contrast agent more quickly than other tissues and masses. The resulting image thus enhances the area of lesions and removes the contrast due to normal tissue.

Two known methods for carrying out DSM are temporal subtraction and dual energy subtraction. Both of these methods can be carried out in DM units.

For the temporal subtraction method, an image of the breast is acquired before the administration of an iodinated contrast agent. This image is known as a pre-contrast image. A contrast agent, for example the iodinated contrast agent, is then intravenously injected into the patient and then a second image is taken. This image is known as the post-contrast image. Software is then used to subtract the pre-contrast image from the post-contrast image with the result being an image where the material in the breast that contains the contrast agent is enhanced. In this procedure, two separate images are taken which means that a patient is exposed to two doses of x-rays.

For the dual energy subtraction method, the pre-contrast image is eliminated and instead two images are taken after the injection of the contrast agent, each image at a different energy and a different instant in time thereby exposing a patient to two doses of X-rays. The two images are taken within typically a fraction of a second from each other after the injection of the contrast agent. One of the images is taken with an x-ray beam having a narrow x-ray energy spectrum centered below the K-edge of the contrast agent and is typically known as the low-energy image. The other image is taken with an x-ray beam having a narrow x-ray energy spectrum centered above the K-edge of the contrast agent and is typically known as the high-energy image. Software is used to subtract the low-energy image from the high-energy image to obtain an image where the material in the breast which contains the contrast agent is enhanced.

Although the effect of the patient's motion is reduced for the dual energy subtraction method compared to the temporal subtraction method, alignment issues of the two images are still existent, for example due to cardiac, respiratory, or patient movement. As previously mentioned, for dual energy subtraction, the low-energy and high-energy images are taken typically within a fraction of a second from each other. Therefore, it would be desirable to have a method for reducing misalignment issues.

Therefore, it is desirable to provide a multi-layer flat panel X-ray detector which allows for two images to be obtained using one x-ray dose.

SUMMARY OF THE DISCLOSURE

The present disclosure relates generally to medical imaging, and in particular, to an apparatus for imaging with energy discrimination in applications such as digital subtraction mammography. It is an aspect of the present disclosure to provide a large area multi-layer flat panel detector design that overcomes at least one of the shortcomings of prior art solutions.

The disclosure is directed at a multi-layer detector, wherein conversion layers are stacked on top of each other so that a single x-ray energy source can be used for multiple images. This reduces or eliminates negative effects due to misalignment of images since the stacked detectors are exposed to the x-ray beam at the same time.

In accordance with another aspect of the disclosure, there is provided a large area flat panel detector including a first conversion layer and a second conversion layer. The first conversion layer is located between a high frequency electromagnetic energy source and the second conversion layer with each conversion layer operable in an integration mode.

In accordance with another aspect of the disclosure, when an x-ray beam is emitted through a patient toward a large area multi-layer flat panel detector having two conversion layers, the first conversion layer acquires low-energy information from the x-ray beam and the second conversion layer acquires high-energy information from the x-ray beam after it has passed through the patient. Alternatively, the first conversion layer may acquire high-energy information while the second conversion layer acquires low-energy information.

In accordance with another aspect of the disclosure, only a single energy beam exposure is required for digital subtraction mammography (DSM). The detector is designed to reduce or eliminate the misalignment effects present in the dual energy subtraction method of DSM as well as reduce or eliminate the need for the patient to be exposed to two energy beam exposures.

Therefore there is provided a novel multi-layer flat panel x-ray detector.

BRIEF DESCRIPTION OF THE DRAWINGS

Embodiments of the present disclosure will now be described, by way of example only, with reference to the attached Figures, wherein.

DETAILED DESCRIPTION OF THE PREFERRED EMBODIMENTS

Figure 1:
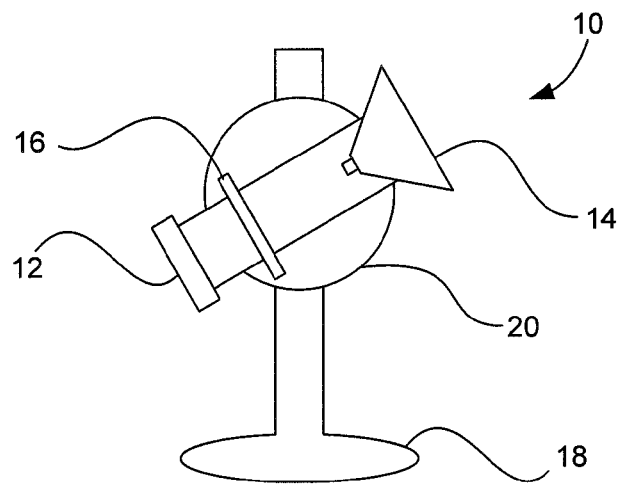
FIG. 1 is a perspective diagram of a digital mammography (DM) unit.

Turning to FIG. 1, a perspective view of a digital mammography (DM) unit is provided. The DM unit 10 includes a multi-layer flat panel detector 12, an x-ray source 14 and a compression paddle 16. The DM unit 10 further includes a stand 18 and a rotating panel 20.

General operation of the DM unit 10 will be understood by one skilled in the art. In operation, the x-ray source 14 emits an x-ray beam, or a series of x-ray beams, towards the flat panel detector 12. The compression paddle 16 is used to compress the patient's breast between the compression paddle 16 and the detector 12. The rotating panel 20 is used to rotate the x-ray source 14, the compression paddle 16 and the detector 12 in order to allow multiple images of the breast to be captured from various positions surrounding the breast.

Figure 2:
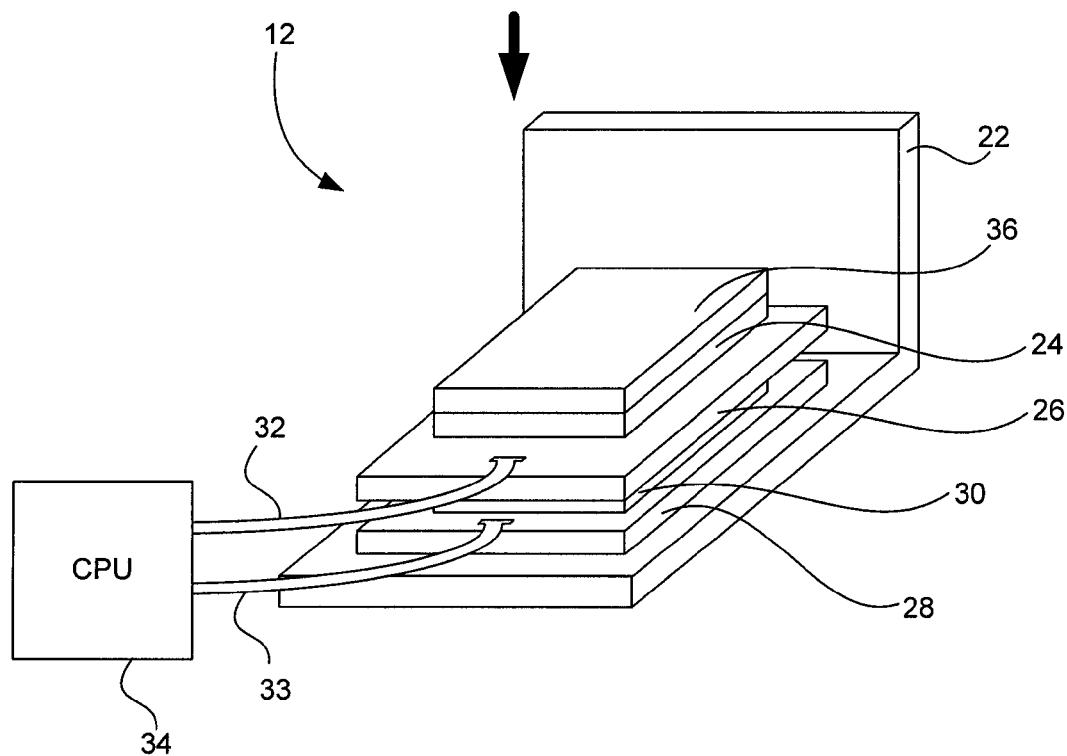
FIG. 2 is a perspective view of a multi-layer flat panel detector for use in a DM unit.

Turning to FIG. 2, a perspective view of a first embodiment of a novel multi-layer flat panel detector for use in the DM unit of FIG. 1 is shown. The flat panel detector 12 includes a housing 22 which, in the figure, is shown opened, or cut away, so that the contents may be seen. As will be understood, the housing 22 encloses the contents of the detector 12. In the current embodiment, the multi-layer flat panel detector 12 further comprises a first direct conversion layer 24, a first printed circuit board (PCB) 24 associated with the first direct conversion layer 24 and a second PCB 28 which is associated with a second direct conversion layer 30. In an alternative embodiment, either one, or both, of the direct conversion layers 24 or 30 may be replaced by indirect conversion layers. The PCBs 26 and 28 each have a cable 32 and 33 which connects the individual PCBs with a processor, or central processing unit (CPU) 34 to pass data between the PCBs 26 and 28 and the processor 34 and to provide the necessary bias voltages to the PCBs required for operation of the detector. In the current embodiment, a collimator 36 is located on top of the first direct conversion layer 24 to collimate the X-ray beams, or photons, from the x-ray source. This optional collimator is preferably integrated perpendicular to the path of the x-rays so that there is less scattering of the x-rays as they pass through the detector 12 and to direct the x-ray photons in a direction parallel to the x-ray beam. The sizes of the direct conversion layers 24 and 30 and the PCBs 26 and 28 may be any size suitable for use as a flat panel detector and does not have to be in the arrangement or in the proportions as shown in FIG. 2.

The thicknesses of the first direct conversion layer and the second direct conversion layer may be chosen to optimize the information that can be acquired from the multilayer detector 12. In the present disclosure, it is possible for the first direct conversion layer 24 to be thinner than the second direct conversion layer 30 since the first direct conversion layer 24 is designed such that it absorbs the low-energy spectrum of the impinging x-ray spectrum or x-ray beams. Due to the required thickness of the second direct conversion layer 30 to absorb the high-energy spectrum of the impinging x-ray spectrum or x-ray beams, the collected electrical signal in the second direct conversion layer 30 may suffer from significant charge trapping. In another embodiment, a Frisch grid may be used in the second direct conversion layer 30 to improve the performance of the second direct conversion layer. In another example, a Frisch grid may also be used in the first direct conversion layer.

Figure 3:
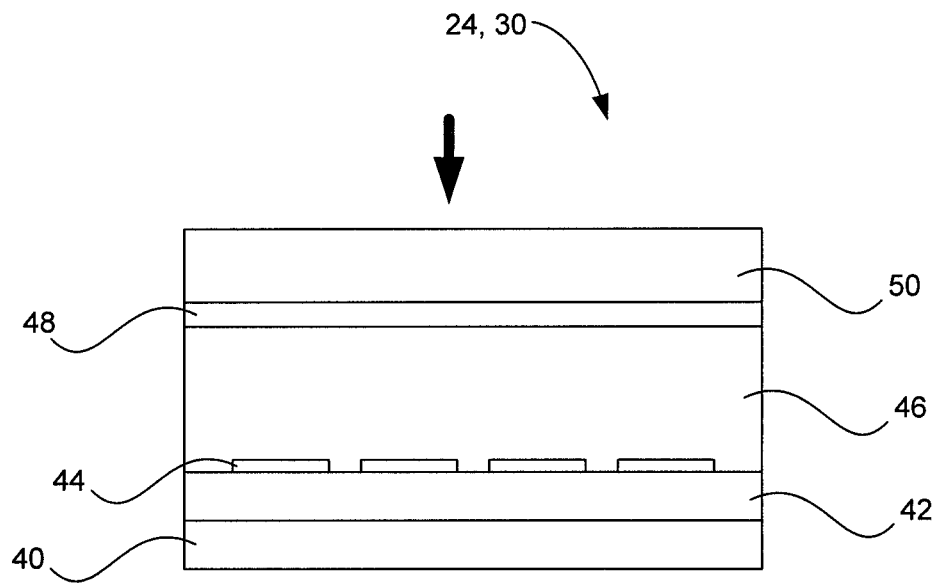
FIG. 3 is a side view of a direct conversion layer for use in the detector of FIG. 2.

Turning to FIG. 3, a schematic diagram of an embodiment of a direct conversion layer is shown. The direct conversion layer 24 or 30 includes a substrate layer 40, preferably glass, which serves as a base for the conversion layer. Atop the substrate layer 40 is a pixel circuit layer 42 on which a set of bottom electrodes 44 are located. The electrodes 44 are sandwiched between the pixel circuit layer 42 and a direct conversion material layer 46. On top of the direct conversion material layer 46 is a top electrode layer 48, preferably transparent, which is then covered by an encapsulation layer 50.

The encapsulation layer 50 is used to reduce or eliminate interaction between the direct conversion material layer 46 and the surrounding environment. The top transparent electrode 48, which in one embodiment may be made of indium tin oxide, is used to create a voltage bias across the direct conversion material layer 46. The direct conversion material layer 46, which in one embodiment may be made of amorphous selenium, is used to convert the x-ray photons to collectable electrical signals. In other words, the direct conversion material layer 46 creates electron-hole pairs from the x-rays being transmitted through the conversion layer 46.

In the current embodiment, the conversion layer 24 or 30 comprises a two-dimensional array of bottom collection electrodes 44, which in one embodiment may be made of aluminum, that collect the charge from the direct conversion material layer 46 and are also used to create a bias across the direct conversion material layer 46 with the top electrode 48. An exemplary array may contain one thousand by one thousand pixel elements, and thus one thousand by one thousand bottom collection electrodes 44. Other pixel and electrode arrangements are also contemplated. The bottom collection electrodes 44 represent the pixels and thus their size determine the spatial resolution of the detector 12. In a preferred embodiment, the dimensions of the bottom collection electrodes 44 are approximately 50 µm by 50 µm.

The pixel circuit layer 42 comprises in-pixel transistors for the readout of the electrical signals collected by the bottom collection electrodes 44. As an example, the in-pixel transistors may form a passive pixel sensor (PPS) or an active pixel sensor (APS) as can be appreciated by one skilled in the art. The substrate layer, such as one made of glass, is used for structural support of the direct conversion layer 24 or 30. Although not shown, the pixel circuit layer is preferably connected to circuitry to transmit the necessary signals representative of the collected electrons, or holes, in order to allow the image to be displayed on a display.

Figure 4:
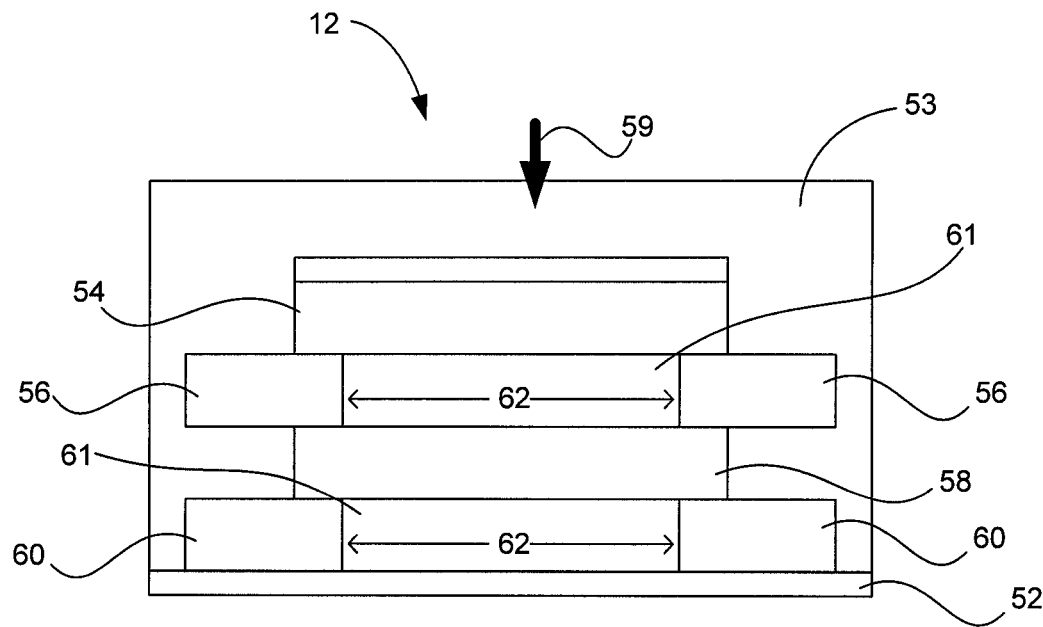
FIG. 4 is a side view of another embodiment of a multi-layer flat panel detector.

Turning to FIG. 4, a front view of another embodiment of a multi-layer flat panel x-ray detector is shown. From the bottom up, the flat panel x-ray detector 12 includes a holding structure 52 which houses the different layers of the detector 12. A backing 53 of the holding structure, or housing is also shown. Atop the structure 52 is a first direct conversion layer 54, although it may be an indirect conversion layer, which is associated with a first PCB 56 and a second direct conversion layer 58, which may also be an indirect conversion layer, which is associated with a second PCB 60. As can be seen, the first and second PCBs 56 and 60 are shaped to allow x-ray photons (represented by arrow 59) to pass directly through the direct conversion layers 54 and 58 as they are located on a periphery of the detector. In other words, there is a gap 61 within the first and second PCBs 26 and 28 where the x-rays may pass through.

In other words, the first PCB 56 and the second PCB 60 are designed such that they will not absorb x-ray photons which are within an area of detection 62 which may be defined as the area in a plane which is parallel to the two-dimensional array of bottom collection electrodes (not shown), and equal in size to the two-dimensional array of the electrodes, and which is centered in the center of the two-dimensional array of the electrodes. The area of detection is thus perpendicular to the x-ray beam.

In an alternative embodiment, the second PCB 60 may be designed such that no piece of the printed circuit board exists in the area of detection below the second direct conversion layer 58 since the x-ray photons that are not absorbed in the first direct conversion layer 54 or the second direct conversion layer 58 are not of interest. One function of the design of the first PCB 56 is to avoid attenuating and scattering x-ray photons that may be absorbed in the second direct conversion layer 58. Such a design of the first PCB 56 is optional, and not necessary in every embodiment of the present disclosure.

Cooling for the detector of the present disclosure may be achieved via air cooling, such as by cooling fans or other known cooling methods. Circuitry or off-pixel algorithms may be used to achieve temperature independence of the acquired images by addressing, for example, the temperature dependence of the in-pixel transistors and direct conversion material characteristics.

Figure 5:
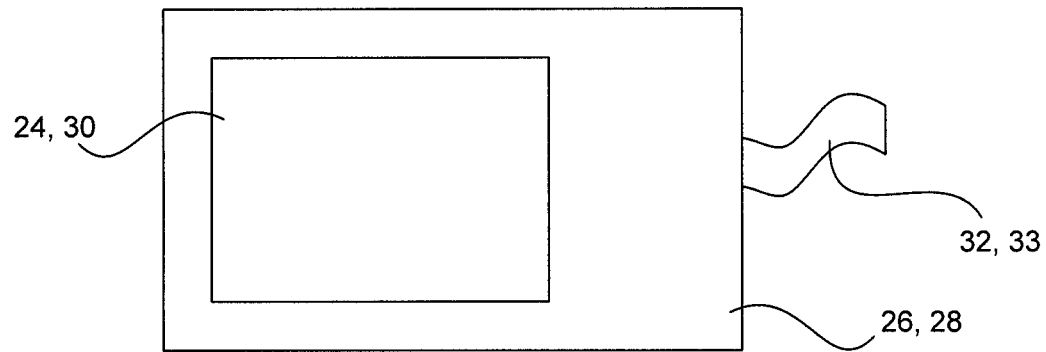
FIG. 5 is a bottom view of a direct conversion layer.
Figure 6:
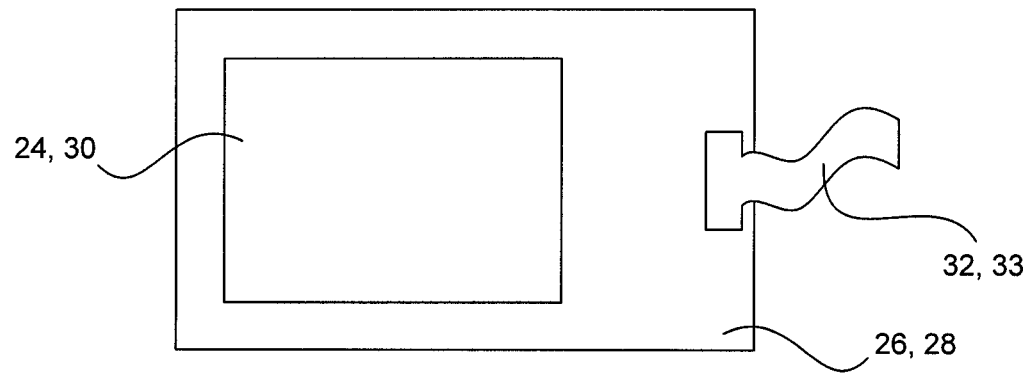
FIG. 6 is a top view of a direct conversion layer.

Turning to FIGS. 5 and 6, top and bottom views of a conversion layer and a PCB are shown.

In one embodiment of operation as described with respect to FIGS. 1 to 3, after the DM unit 10 is set up and the patient positioned with their breast against the DM unit, the x-ray source 14 is activated and x-rays are transmitted towards the patient. The x-ray photons travel or pass through the patient in the direction of the flat panel detector 12.

After receiving the photons, the first direct conversion layer 24 generates an electrical signal that is proportional to the intensity of the low-energy portion of the x-ray photon spectrum which has passed through the patient. The x-ray photons then continue towards the second direct conversion layer 30 which generates an electrical signal that is proportional to the intensity of the high-energy portion of the x-ray photon spectrum which has passed through the patient. The electrical signals produced by the first direct conversion layer 24 are transmitted to, or acquired by, the circuitry on the first PCB 24 and then passed to the processor 34 via the first electronics cable 32. The electrical signals produced by the second direct conversion layer 30 are transmitted to, or acquired by the circuitry on the second PCB 28 and passed to the processor 34 via the second electronics cable 33. Once the electrical signals produced by the first direct conversion layer 24 and the second direct conversion layer 30 are acquired by the processor 34, the signals are subsequently processed, for example to create a digital subtraction mammography (DSM) image or other image or images which may be used for diagnosis or treatment. With the use of an injected contrast agent, the electrical signals produced by the first direct conversion layer 24 and the second direct conversion layer 30 may provide sufficient information to create a DSM image wherein the areas of contrast agent accumulation in the patient will have greater contrast compared to other regions, for example regions of soft tissue.

After obtaining the images or signals, the low and high energy images are combined using a logarithmic weighted subtraction method, although other methods may be used to obtain a combined image. The images obtained by each conversion layer 24 or 30 are pixelated, wherein each pixel has a corresponding signal level. In the logarithmic weighted subtraction method, the dual-energy signals are obtained by the subtraction of the natural logarithm of the high-energy signals with a weight factor multiplied by the natural logarithm of the low-energy signals represented by the equation:

$$I_{DE} = \ln(I_H) - w \ln(I_L)$$

where $I_{DE}$ represent the dual-energy signals, $I_H$ represents the high-energy signals, $I_L$ represents the low-energy signals, and w represents the weight factor. The low and high energy signals correspond to the signals which have been produced by matching pixels on the top and bottom conversion layers.

The choice of weight factor is a factor for achieving a high-quality subtracted image. The weight factor is chosen to minimize the contrast of the soft tissue and the anatomical background noise.

In one example, the optimal weight function may be determined by minimizing the anatomical noise defined by the following equation:

$$\delta(w) = \left( \frac{1}{n-1} \sum_{1}^{n} (I_{DE}(g_i, w) - \overline{I_{DE}(w)})^2 \right)^{1/2}$$

where w is the weight factor, $g_i$ is the glandularity (i.e. the fraction of breast tissue that is glandular) of sample i, $I_{DE}(g_i, w)$ is the dual-energy signal passing through a breast of glandularity $g_i$ using a weight factor of w, $I_{DE}(w)$ is the dual-energy signal averaged over all glandularities, and n is the number of different glandularity samples. The optimal weight factor is dependent on the breast thickness and thus can be determined for breasts of different compressed thicknesses.

The resulting value for $I_{DE}$ provides an image which may be used in the determination as to whether there is any tumour within the body part, such as a woman's breast, being imaged.

One advantage of the novel disclosure allows the creation of DSM images with the patient only being subjected to a single x-ray exposure. As a comparison, the prior art dual energy subtraction or temporal subtraction methods for DSM require the patient to be exposed to x-rays multiple times, thus the benefit of the present disclosure can be appreciated by those skilled in the art. Although the present disclosure is a multi-layer detector as opposed to a single layer detector, it may also be used for the dual energy subtraction or temporal subtraction methods for DSM.

To achieve these DSM methods, a single layer of the multi-layer detector, for example either the first direct conversion layer 24 or the second direct conversion layer 30, may be read out while the other layer of the multi-layer detector is not read out. In this exemplary usage, the multi-layer flat panel detector may operate as a single layer detector.

A single exposure DSM image may also be acquired using the system or apparatus of the present disclosure, which reduces the misalignment effects compared to the currently known dual energy subtraction and temporal subtraction methods for DSM. As an example, with a single exposure of an x-ray beam, the first direct conversion layer 24 may obtain the low-energy information from the beam and the second direct conversion layer 30 may obtain the high-energy information from the beam. The voltage of the x-ray source is selected to allow the first direct conversion layer 24 to obtain an image that is representative of an image taken without the contrast agent, and to allow the second direct conversion layer 30 to obtain an image that is representative of an image taken after the contrast agent has been administered. The image which is representative of an image taken without the contrast agent resembles an image taken using a low-energy x-ray beam after the contrast agent has been administered since the contrast agent does not significantly attenuate low-energy x-ray photons. The image which is representative of an image taken after the contrast agent has been administered resembles an image taken using a high-energy x-ray beam after the contrast agent has been administered since the contrast agent significantly attenuates high-energy x-ray photons. After obtaining the images, subtraction of the images may be performed to produce a DSM image.

Figure 7:
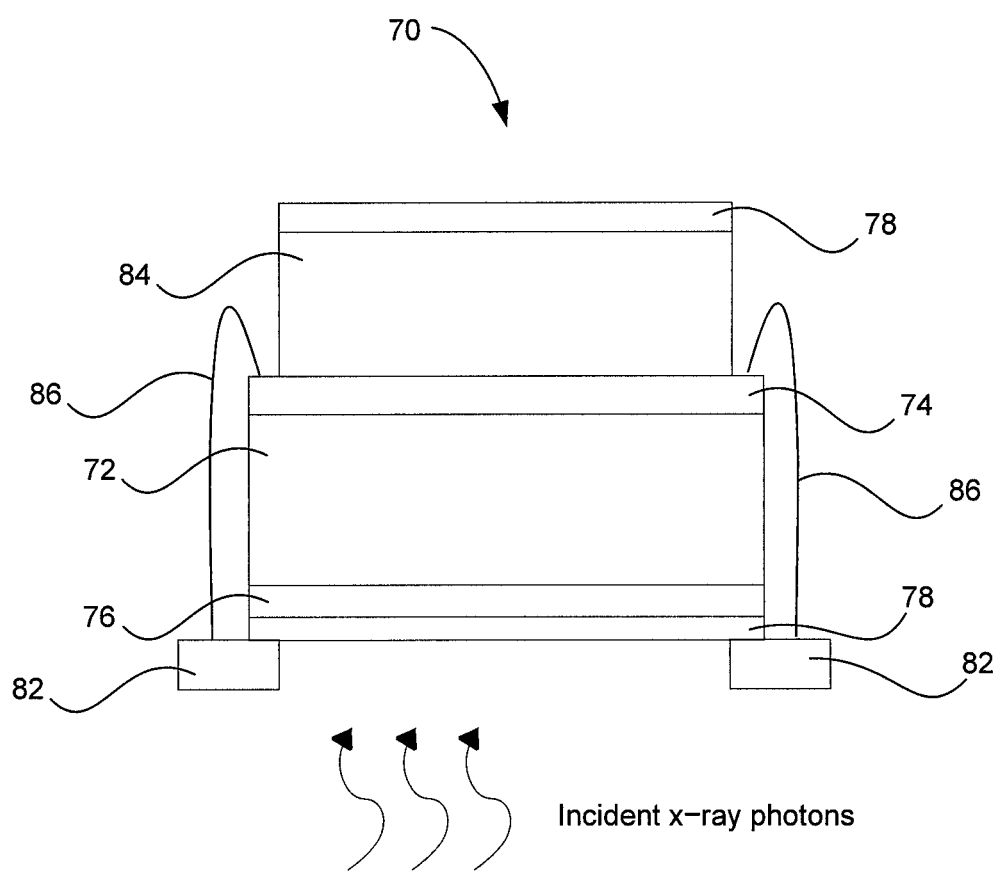
FIG. 7 is a schematic view of another embodiment of a multi-layer flat panel detector.

Turning to FIG. 7, a schematic diagram of another embodiment of a multi-layer flat panel X-ray detector is shown. The detector 70 includes a silicon wafer portion 72 or a first conversion layer, either direct or indirect, which is sandwiched between a printed circuit board 74 including a set of thin-film transistors, read-out and control lines and electrodes and an a-Si:H intrinsic layer or n-type layers or combination of both 76. Instead of an actual PCB 74, the set of thin-film transistors, read-out and control lines and electrodes may be integrated in the silicon wafer 72. A metal electrode 78 is located on the other side of the a-Si:H intrinsic layer 76, for biasing the detector, with a PCB 82 below that. On the other surface of the PCB 74, is a direct conversion material 84 or a second conversion layer, either direct or indirect, which is then capped by a second metal electrode 78. Alternatively, the direct conversion material 84 may be deposited directly on the first conversion layer. In this manner a glass substrate is not required for the second conversion layer and the read-out and control lines from both conversion layers are located within the same plane, easing the requirements for bonding and only requiring the use of a single printed circuit board 74. The second PCB 82 is in communication with the first PCB 74 or readout electronics. Another advantage of this embodiment is that there may be a reduced amount of or no bonding to connect the first and second conversion layers, or misalignment of the first and second conversion layers during their connection. Another benefit of this embodiment is that fabrication and implementation costs may be reduced.

Figure 8:
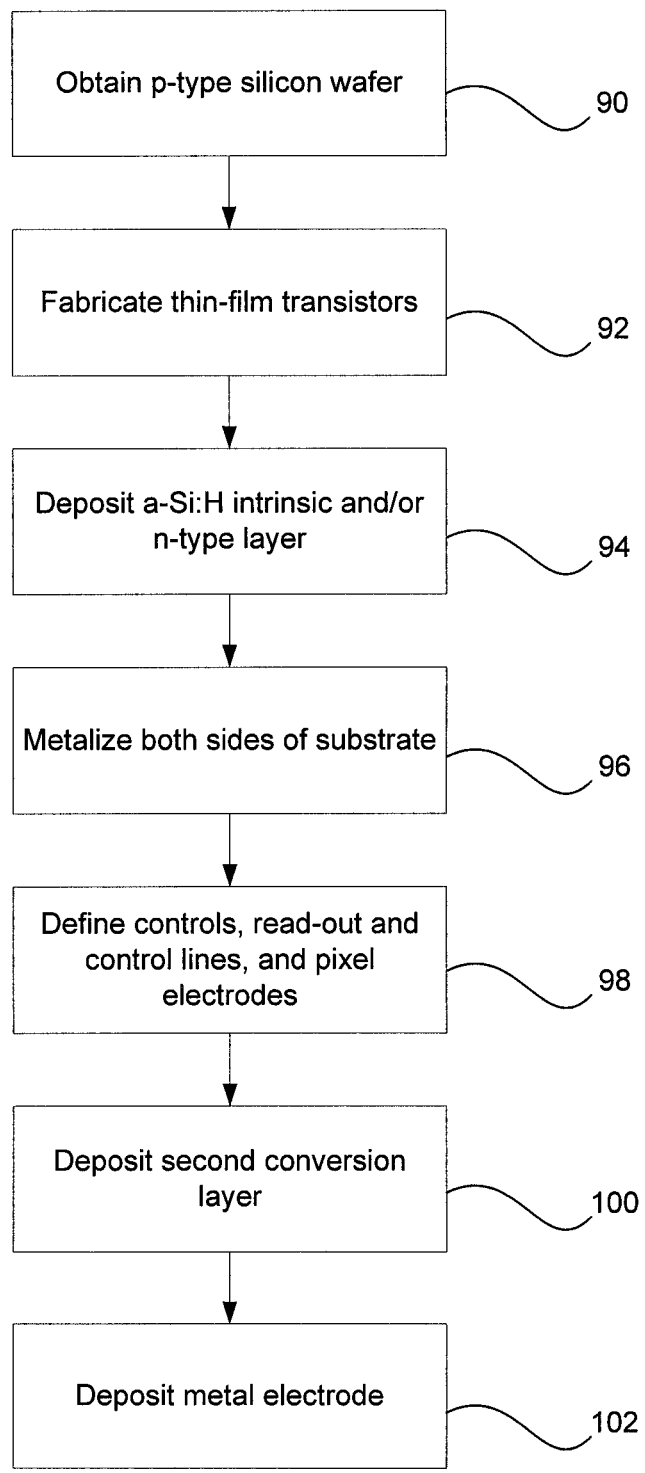
FIG. 8 is a flowchart outlining a method of fabricating a multi-layer flat panel detector of FIG. 7.

Turning to FIG. 8, a method of fabricating a detector as disclosed in FIG. 7 is shown. A lightly doped p-type bulk silicon crystalline silicon wafer is obtained 90 and processed by fabricating 92 the thin-film transistors on the wafer. Next, intrinsic and n-type hydrogenated amorphous silicon (a-Si:H) layers are added 94, forming an p-i-n structure, though it is also possible to ignore the intrinsic layer and instead form a p-n structure. A metallic electrode is then deposited over the n-type a-Si:H film. The read-out and control lines are fabricated 98 on the other side of the silicon wafer (over the thin-film transistors). During this process the read-out and control lines and the pixel electrodes for the second conversion layer may also be patterned if the second conversion material is to be deposited 100 upon the first conversion layer (which is comprised of the silicon wafer, the intrinsic and/or n-type a-Si:H layers, the thin-film transistors, and the read-out and control lines). In this embodiment, the second conversion material would be deposited on top of the second conversion layer pixel electrodes. A metal electrode is then deposited 102 to cover the second conversion material or second conversion layer. If the second conversion layer is bonded to the first conversion layer, the read-out and control lines and the second conversion pixel electrodes may first be deposited on the second conversion material. If the second conversion material is a self-supporting solid crystal or amorphous structure which does not have an affixed substrate, a metal contact may be deposited on the side of the second conversion material which is opposite to the side which will be bonded to the first conversion layer. If the second conversion material is supported through the use of a substrate, a metal electrode may be deposited between the second conversion material and the substrate. The first conversion layer and second conversion layer may be bonded together using standard bonding techniques.

Figure 9:
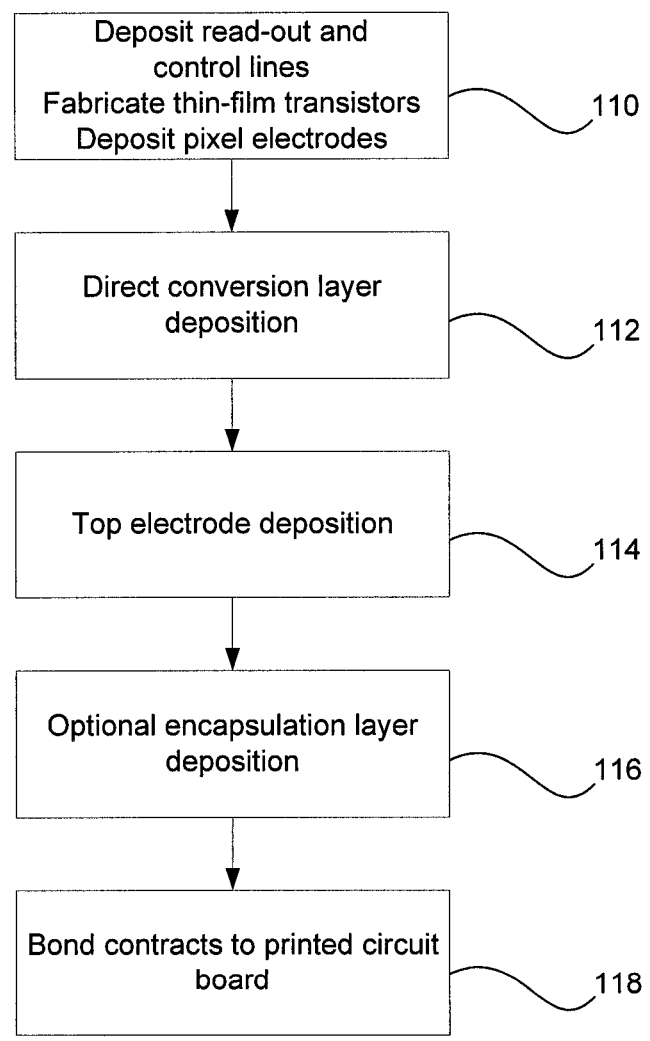
FIG. 9 is a flowchart outlining a method of fabricating a multi-layer flat panel detector of FIG. 2.

Turning to FIG. 9, a flowchart outlining a method of fabricating a stacked flat-panel detector is shown. In the current embodiment, the conversion material is amorphous selenium. On top of a glass substrate, a set of thin-film transistors, read-out and control lines, and bottom electrodes are patterned 110 using standard lithography techniques to provide the necessary components to transmit the collected information to a processor to display the captured image. A direct conversion material is then deposited on top of the bottom electrodes 112. The thickness of this conversion material is determined by the manufacturer based on criteria such as, but not limited to, flat panel applications. A top electrode is then deposited 114 on top of the direct conversion material. An optional top encapsulation layer may then be deposited 116 over the transparent top electrode to aid in the longevity of the detector. The read-out and control lines of the direct conversion layer are then connected 118 to a printed circuit board via wire bonding techniques. The same technique as described above may be used to fabricate the second layer of the flat-panel detector.

Once both pieces (i.e. the first and second layers of the flat-panel detectors) have been fabricated, the first conversion layer is mounted on top of the second conversion layer. Alignment of these two layers with each other is beneficial as the subtracted image is obtained by the subtraction of the pixelated signals and assumes that perfect alignment has been achieved. Misalignment correction techniques may be used during the processing of the images to reduce the effects of misalignment of the two layers.

Figure 10:
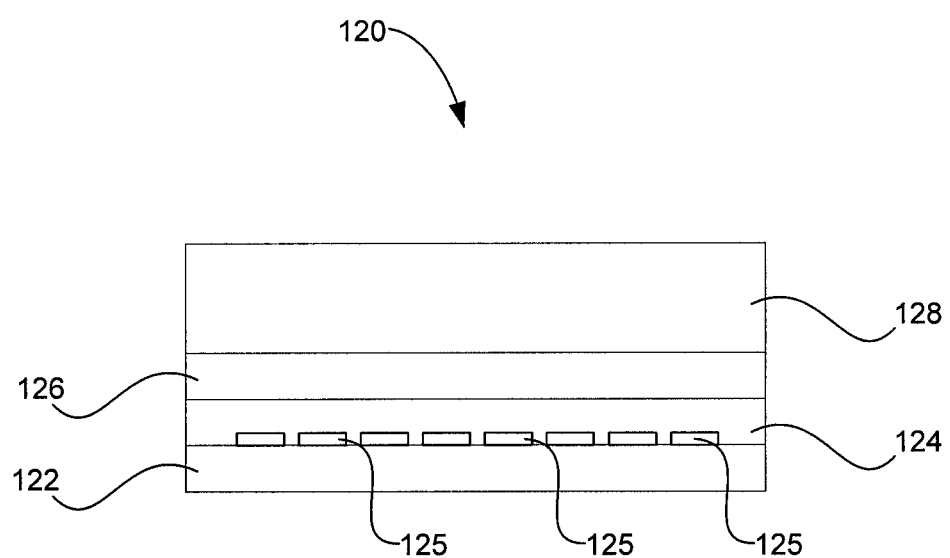
FIG. 10 is a schematic diagram of an embodiment of an indirect conversion layer for use with a multi-layer flat panel detector.

Turning to FIG. 10, a schematic diagram of an indirect conversion layer for use in a multi-layer flat panel detector is shown. The indirect conversion layer 120 may replace the direct conversion layer within the detector. The indirect conversion layer 120 includes a substrate layer 122 which acts as a foundation for the entire indirect conversion layer 120. On top of the substrate layer 122 is a pixel circuit layer 124 which includes the circuitry 125 or electrical components, such as thin-film transistors; readout lines and control lines, for reading out the signals which are collected by the conversion layer 120 and then transmits the signals to a set of readout electronics so that the collected image can be displayed on a display or use in DSM. On top of the pixel circuit layer 124 is a photodiode layer 126 with a scintillator layer 128 on top of the photodiode layer 126. In one embodiment, the scintillator layer 128 may be made of thallium doped cesium iodide (CsI:Tl). In another embodiment, the photodiodes may be made within a-Si:H p-i-n photodiodes.

Therefore, within a multi-layer flat panel detector, at least two indirect conversion layers are used. In operation, the scintillator layer converts the x-ray photons from the x-ray source into optical photons, which may be defined as photons with frequencies within or near the visible spectrum. These optical photons then pass through the scintillator layer and are absorbed by the pixilated photodiode layer 126. While passing through the photodiode layer, the x-ray photons are converted into electron-hole pairs and collected by the photodiode. The signals which are collected by the photodiodes are then transmitted via the pixel circuit layer 124 to a PCB.

In yet a further embodiment, the multi-layer flat panel detector comprises one indirect conversion layer and one direct conversion layer. As will be understood, each one of these layers is associated with circuitry for reading out the signlas which are detected by the detector so that they may be displayed.

The present disclosure can find use in several applications. In mammography, the multi-layer flat panel detector may be used for digital subtraction, digital subtraction tomosynthesis, or fluoroscopy. The present disclosure may also find use in security x-ray applications for screening using x-rays where energy discrimination may be desirable or any application where energy integrating detectors capable of energy discrimination are desirable. In the present disclosure, indirect conversion layers may be used instead of direct conversion layers if preferable, to suit the application, the cost requirements or both. The dual layer nature of the present disclosure allows more information to be extracted from an x-ray beam compared to a single layer detector due to the use of multiple direct conversion layers. Thus, the present disclosure may replace flat panel single layer detectors in applications where the desire for energy discrimination exists.

The above-described embodiments of the disclosure are intended to be examples only. Alterations, modifications and variations can be effected to the particular embodiments by those of skill in the art without departing from the scope of the disclosure, which is defined solely by the claims appended hereto.

What is claimed is:

1. A multi-layer flat panel detector for digital X-ray imaging comprising:
    a single substrate layer;
    a first conversion layer configured to detect radiation from an x-ray source including a first conversion layer conversion material layer and a first conversion layer pixel layer, the first conversion layer on a first side of the single substrate layer;
    a second conversion layer configured to detect radiation from the x-ray source including a second conversion layer conversion material layer and a second conversion layer pixel layer, the second conversion layer on a side of the single substrate layer opposite the first side of the single substrate layer;
    a printed circuit board for receiving signals generated by the first or second conversion layers, wherein the single substrate layer is the printed circuit board;
    a set of readout electronics, the read out electronics integrated within the printed circuit board; and
    a processor for processing the signals to produce an image being generated;
    wherein the first conversion layer pixel layer and the second conversion layer pixel layer each include in-pixel transistors embedded within and share the set of readout electronics.

2. The multi-layer flat panel detector of claim 1 wherein the first conversion layer absorbs a low-energy spectrum and the second conversion layer absorbs a high-energy spectrum.

3. The multi-layer flat panel detector of claim 1 wherein the first conversion layer absorbs a high-energy spectrum and the second conversion layer absorbs a low-energy spectrum.

4. The multi-layer flat panel detector of claim 1 further comprising a collimator for collimating x-ray photons which are directed at the detector.

5. The multi-layer flat panel detector of claim 4 wherein the x-ray photons are collimated to be perpendicular to the first conversion layer.

6. The multi-layer flat panel detector of claim 1 wherein the first conversion layer further comprises:
    a first conversion layer top electrode layer; and
    a first conversion layer encapsulation layer.

7. The multi-layer flat panel detector of claim 6 wherein the first conversion layer top electrode layer is a transparent top electrode layer.

8. The multi-layer flat panel detector of claim 1 wherein the single substrate layer is a glass substrate layer.

9. The multi-layer flat panel detector of claim 1 wherein the first and second conversion layers are direct conversion layers.

10. The multi-layer flat panel detector of claim 1 wherein the first and second conversion layers are indirect conversion layers.

11. The multi-layer flat panel detector of claim 1 wherein the first conversion layer is a direct conversion layer and the second conversion layer is an indirect conversion layer.

12. The multi-layer flat panel detector of claim 1 wherein the first conversion layer is an indirect conversion layer and the second conversion layer is a direct conversion layer.

13. A mammography unit comprising:
    a x-ray source;
    a multi-layer flat panel detector; and
    a compression panel;
    wherein the multi-layer flat panel detector includes:
        a single substrate layer;
        a first conversion layer configured to detect radiation from the x-ray source including a first conversion layer conversion material layer and a first conversion layer pixel layer, the first conversion layer on a first side of the single substrate layer;
        a second conversion layer configured to detect radiation from the x-ray source including a second conversion layer conversion material layer and a second conversion layer pixel layer, the second conversion layer on a side of the single substrate layer opposite the first side of the single substrate layer;
        a printed circuit board for receiving signals generated by the first or second conversion layers, wherein the single substrate layer is the printed circuit board;
        a set of readout electronics, the read out electronics integrated within the printed circuit board; and
        a processor for processing the signals to produce an image being generated;
        wherein the first conversion layer pixel layer and the second conversion layer pixel layer each include in-pixel transistors embedded within and share the set of readout electronics.

14. The mammography unit of claim 13 wherein the first and second conversion layers are direct conversion layers.

15. The mammography unit of claim 13 wherein the first and second conversion layers are indirect conversion layers.

16. The mammography unit of claim 13 wherein the first conversion layer is a direct conversion layer and the second conversion layer is an indirect conversion layer.

17. The mammography unit of claim 13 wherein the first conversion layer is an indirect conversion layer and the second conversion layer is a direct conversion layer.

18. The multi-layer flat panel detector of claim 1 wherein the in-pixel transistors form a passive pixel sensor or an active pixel sensor.

19. The multi-layer flat panel detector of claim 1 wherein the first and second conversion layers are deposited directly onto the single substrate layer.

\* \* \* \* \*